US00PP16479P3

(12) United States Plant Patent
van der Voort

(10) Patent No.: US PP16,479 P3
(45) Date of Patent: Apr. 25, 2006

(54) LILY PLANT NAMED 'CONCA D'OR'

(50) Latin Name: *Lilium L. oriental*
Varietal Denomination: Conca D'or

(75) Inventor: Cees A. van der Voort, Katwijk (NL)

(73) Assignee: Vletter & Den Haan Beheer B.V., Rijnsburg (NL)

( * ) Notice: Subject to any disclaimer, the term of this patent is extended or adjusted under 35 U.S.C. 154(b) by 31 days.

(21) Appl. No.: 10/607,304

(22) Filed: Jun. 27, 2003

(65) Prior Publication Data

US 2004/0123358 P1 Jun. 24, 2004

Related U.S. Application Data

(60) Provisional application No. 60/392,041, filed on Jun. 28, 2002.

(51) Int. Cl.
*A01H 5/00* (2006.01)

(52) U.S. Cl. ..... Plt./315

(58) Field of Classification Search ..... Plt./315
See application file for complete search history.

(56) References Cited

FOREIGN PATENT DOCUMENTS

| | | |
|---|---|---|
| AU | 2425 | 3/2004 |
| NZ | 2003 | 9/2002 |
| PL | 0 1895 | 2/2004 |
| QZ | 8444 | 11/2001 |
| ZA | 20032848 | 3/2003 |

OTHER PUBLICATIONS

UPOV hits, UPOV–rom, Plant Genome Database, May 2003.*

* cited by examiner

*Primary Examiner*—Anne Marie Grunberg
(74) *Attorney, Agent, or Firm*—Foley & Lardner, LLP

(57) ABSTRACT

A new and distinct cultivar of lily plant named 'Conca D'or' characterized by its large, upright light yellow flowers with darker yellow center and contrasting orange pollen, and vigorous growth.

1 Drawing Sheet

Latin name of the genus and species of the plant claimed: *Lilium L. oriental* hybrid.
Variety denomination: Conca D'or.

BACKGROUND OF THE INVENTION

The present invention comprises a new and distinct cultivar of lily plant, botanically known as *Lilium L.,* and hereinafter referred to by the cultivar name 'Conca D'or'.

'Conca D'or' is a product of a planned breeding program which had the objective of creating new lily cultivar having many large upright flowers and vigorous growth habit.

'Conca D'or' originated from a hybridization made by the inventor, Cees A. van der Voort, in a controlled breeding program in Rijnsburg, the Netherlands in October, 1995. The parental cultivars are proprietary *Lilium L.* seedlings designated 'Aubade' and 'PH95-40' (unpatented).

'Conca D'or' was discovered and selected as one flowering plant within the progeny of the stated cross by the inventor, in October, 1995 in a controlled environment in Rijnsburg, the Netherlands.

The first act of asexual reproduction of 'Conca D'or' was accomplished when scales were taken from the initial selection in a controlled environment in Rijnsburg, the Netherlands by, or under the supervision of, Cees A. van der Voort. Horticultural examination of selected plants has demonstrated that the combination of characteristics as herein disclosed for 'Concor D'or' are firmly fixed and are retained through successive generations of asexual reproduction.

BRIEF DESCRIPTION OF THE INVENTION

The following traits have been repeatedly observed and are determined to be basic characteristics of 'Conca D'or' which in combination distinguish this lily as a new and distinct cultivar:

1. large, upright light yellow flowers with darker yellow center and contrasting orange pollen; and
2. vigorous growth habit.

In comparison to the parental cultivar 'Aubade', the flowers of 'Conca D'or' are side-facing, whereas the flowers of 'Aubade' are upward facing. The flowers of both 'Conca D'or' and the parental plant 'PH95-40' are more of an intense yellow color than the flowers of 'Aubade'. The stems of both 'Conca D'or' and 'PH95-40' are taller than those of 'Aubade'. 'Conca D'or' has a more vigorous growth habit than both parental cultivars.

Of the many commercial cultivars known to the present inventor, the most similar in comparison to 'Conca D'or' is the parental cultivar 'Aubade'.

BRIEF DESCRIPTION OF THE DRAWING

The accompanying color photographic drawing shows a typical plant of 'Conca D'or', with colors being as true as possible with illustrations of this type. The drawing shows the large, upright light yellow flowers with darker yellow center and contrasting orange pollen, and the buds, and leaves of the plant.

DETAILED BOTANICAL DESCRIPTION

The following observations, measurements and values describe the new cultivar as grown in Rijnsburg, The Netherlands under conditions which closely approximate those generally used in commercial practice. The plants were grown under controlled climate conditions in a greenhouse. Color references are made to The Royal Horticultural Society (R.H.S.) Colour Chart (publication date 2001), except where general colors of ordinary significance are used. Color values were taken under daylight conditions at approximately 12:00 pm in Rijnsburg, The Netherlands. The age of the plant described is about 90 days.

Parentage:

*Male parent.*—Propriety seedling designated 'Aubade' (unpatented).

*Female parent.*—Propriety seedling designated 'PH95-40'.

Propagation: Scales were taken from the bulbs.

Plant:

General appearance and form:

*Height.*—Medium, 90 cm, depending on growing conditions.

*Flowering season.*—All year round in controlled climate conditions in the greenhouse.

*Winter hardiness/weather tolerance.*—None.

*Lastingness of the individual bloom.*—21 days, depending on storing conditions.

*Rooting habit.*—Vigorous.

*Fragrance.*—Strong, typical to lily plants.

Stem description:

*Length.*—Medium, 90 cm., depending on growing conditions.

*Diameter.*—2.5 mm.

*Strength.*—Strong.

Foliage:

*Overall shape of leaf.*—Ovate.

*Quantity.*—Approximately 35–45, depending on growing conditions.

*Length.*—Medium to long, 8.5 cm, depending on growing conditions.

*Width.*—Medium to wide, 2.5 cm, depending on growing conditions.

*Texture.*—Hardly any pubescence.

*Color of upper surface.*—Mature leaf: Dark green — RHS 136A. Immature leaf: Medium green — RHS 136B.

*Color of lower surface.*—Mature leaf: Medium green. Immature leaf: Medium green.

*Venation color.*—Upper surface: Medium green. Lower surface: Medium green.

*Petiole.*—Length: 2.5 mm. Color: Medium green.

Flowers:

*Flower type and habit.*—Raceme.

*Flower diameter.*—14 cm.

*Overall shape.*—Hexagonal star; bowl-shaped in cross-section.

*Average number of flowers per lateral branch.*—4, depending on growing conditions.

*Tepals.*—Number of tepals: 6. Texture: Papillose. Tepal size: Length: Medium to long, 3.5 cm. Width: Medium to wide, 5 cm. Tepal Color: Upper surface: Yellow, between RHS 9B and RHS 12B. Lower surface: Light yellow, RHS 9D.

Bud:

*Form.*—Tapering.

*Color.*—Light yellowish-green, RHS 154D.

*Length.*—8 cm, depending on growing conditions.

*Diameter.*—2.5 depending on growing conditions.

*Peduncles:* 6 cm length, horizontal to upright angle, medium green in color.

Reproductive organs:

*Stamen.*—Number: 6. Color: Yellowish green RHS 154B.

*Seeds.*—None.

*Fruit.*—None.

*Anthers.*—Number: 6. Color: Green.

*Pollen.*—Color: Greyed red RHS178C. Stigma: Number: 1. Color: Dark purple.

Disease/pest resistance/susceptibility: No known information.

I claim:

1. A new and distinct cultivar of lily plant named 'Conca D'or', as illustrated and described herein.

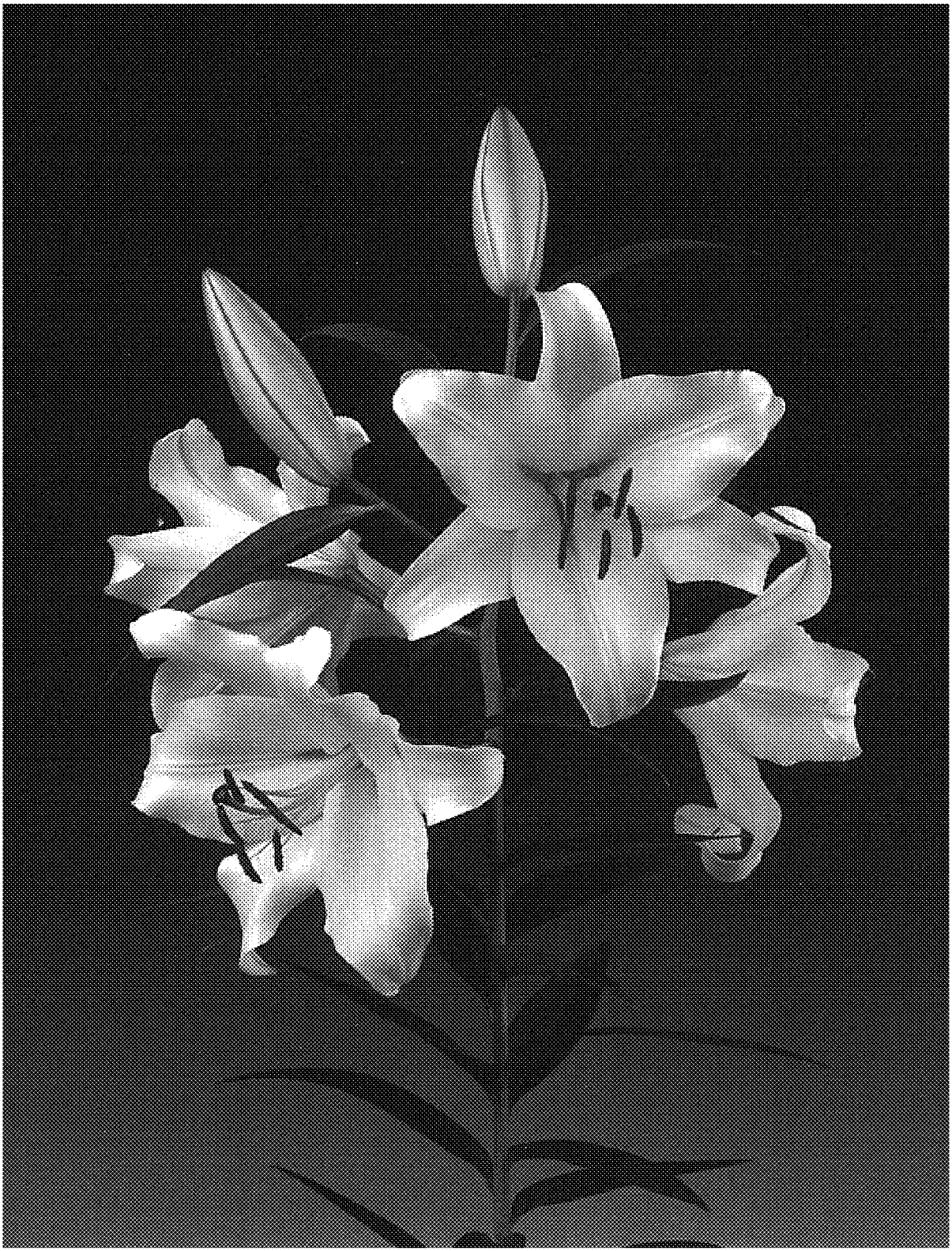

* * * * *